United States Patent
Tibbs et al.

(10) Patent No.: US 9,241,956 B2
(45) Date of Patent: Jan. 26, 2016

(54) PHARMACEUTICAL PREPARATION AND METHOD FOR TREATMENT OF DIABETES

(71) Applicants: Kenneth John Tibbs, Benson, AZ (US); Dawn Ann Tibbs, Benson, AZ (US)

(72) Inventors: Kenneth John Tibbs, Benson, AZ (US); Dawn Ann Tibbs, Benson, AZ (US)

(*) Notice: Subject to any disclaimer, the term of this patent is extended or adjusted under 35 U.S.C. 154(b) by 0 days.

(21) Appl. No.: 14/579,011

(22) Filed: Dec. 22, 2014

(65) Prior Publication Data

US 2015/0110881 A1    Apr. 23, 2015

Related U.S. Application Data

(63) Continuation-in-part of application No. 14/066,537, filed on Oct. 29, 2013, now abandoned.

(60) Provisional application No. 61/796,200, filed on Nov. 5, 2012.

(51) Int. Cl.

| | |
|---|---|
| *A61K 33/10* | (2006.01) |
| *A61K 9/28* | (2006.01) |
| *A61K 45/06* | (2006.01) |
| *A61K 31/155* | (2006.01) |
| *A61K 33/08* | (2006.01) |
| *A61K 33/34* | (2006.01) |
| *A61K 9/20* | (2006.01) |
| *A61K 9/50* | (2006.01) |

(52) U.S. Cl.
CPC .............. *A61K 33/10* (2013.01); *A61K 31/155* (2013.01); *A61K 33/08* (2013.01); *A61K 33/34* (2013.01); *A61K 45/06* (2013.01); *A61K 9/2081* (2013.01); *A61K 9/286* (2013.01); *A61K 9/288* (2013.01); *A61K 9/2846* (2013.01); *A61K 9/2866* (2013.01); *A61K 9/5026* (2013.01); *A61K 9/5036* (2013.01); *A61K 9/5042* (2013.01); *A61K 9/5063* (2013.01)

(58) Field of Classification Search
None
See application file for complete search history.

(56) References Cited

U.S. PATENT DOCUMENTS

2011/0280945 A1*  11/2011  Lebon et al. ............... 424/494

FOREIGN PATENT DOCUMENTS

| WO | WO 2008069788 A1 * | 6/2008 | ............... A23L 2/00 |
| WO | WO 2010055268 A1 * | 5/2010 | ............... A61K 9/50 |
| WO | WO 2010068907 A2 * | 6/2010 | ............. A61K 38/28 |

OTHER PUBLICATIONS

Potur et al., "Optimization by experimental design of an immediate release tablet formulation comprising metformin and glibenclamide", 2011, Farmacia, vol. 59, No. 5, pp. 690-699.*
Nachum et al., "Twice daily versus four times daily insulin dose regimens for diabetes in pregnancy: randomised controlled trial", Nov. 6, 1999, British Medical Journal, vol. 319, pp. 1223-1227.*

* cited by examiner

*Primary Examiner* — Michael B Pallay
(74) *Attorney, Agent, or Firm* — IDP Patent Services; Olav M. Underdal

(57) ABSTRACT

A pharmaceutical composition for use in oral medication for the treatment of diabetes mellitus can include an antacid agent with an enteric coating, which permits the antacid agent to be delivered in the small intestine where it reduces acidity thereby causing a lowering of blood sugar levels. The pharmaceutical composition can be packaged in various tablet forms, including standard tablets and multiple pellet tablets. The pharmaceutical composition can further include a composition for treatment of diabetes, such as metformin, in enteric or non-enteric formulations. The pharmaceutical composition can further include an enteric-coated gastric acid secretion inhibitor. Also disclosed are methods for the treatment of diabetes mellitus, using the pharmaceutical composition and its variants.

20 Claims, 5 Drawing Sheets

PHARMACEUTICAL PREPARATION AND METHOD FOR TREATMENT OF DIABETES

CROSS-REFERENCE TO RELATED APPLICATIONS

This application is a Continuation-In-Part of U.S. Non-Provisional application Ser. No. 14/066,537, filed Oct. 29, 2013, which claims the benefit of U.S. Provisional Application No. 61/796,200, filed Nov. 5, 2012.

FIELD OF THE INVENTION

The present invention relates generally to the field of medications and related methods for the treatment of diabetes mellitus, and more specifically to a novel pharmaceutical composition and delivery method that can be used as a primary or adjunct therapy for treatment of diabetes mellitus type I and type II.

BACKGROUND OF THE INVENTION

Diabetes mellitus, also commonly referred to as diabetes, is a group of metabolic diseases in which a person has high blood sugar, either because the pancreas does not produce enough insulin, or because cells do not respond to the insulin that is produced. This high blood sugar produces the classical symptoms of polyuria (frequent urination), polydipsia (increased thirst) and polyphagia (increased hunger).

All forms of diabetes are associated with increased risk of long-term serious health complications. These may typically develop after several years of diabetes. The major long-term complications relate to various manifestations of damage to blood vessels. Such manifestations include eye diseases, cardiovascular diseases, ischemic heart disease, including angina and myocardial infarction, stroke and peripheral vascular disease. A related risk is diabetic neuropathy, the impact of diabetes on the nervous system, which can cause numbness, tingling and pain in the feet, and eventually lead to diabetes-related foot problems, such as diabetic foot ulcers, that can be difficult to treat and in some cases can require amputation.

There are two major types of diabetes. Type 1 diabetes is partly inherited and unrelated to lifestyle, and generally at its outset can be triggered by certain infections. Patients will often acquire type 1 diabetes at a young age. Type 2 diabetes is primarily caused by certain lifestyle factors, including obesity, lack of physical activity, and poor diet, and is often associated with old age.

Globally, as of 2010, it was estimated that almost 300 million people had diabetes, with type II accounting for approximately 90% of the cases. Diabetes is recognized as an evolving global epidemic with an expectation that the number of cases will double from 2010 to 2030. Diabetes is common throughout the world, but is more prevalent in developed countries. It is expected that the growth rate of diabetes type II will be largest in Asia and Africa, as developing nations on these continents become more urbanized, and adopt a "westernized" lifestyle and diet, so that nations in these countries will eventually form the majority of new cases of diabetes mellitus.

In conjunction with the rapid worldwide growth of diabetes, it is an increasing global health management risk that many cases of diabetes remain undiagnosed until a late stage, and particularly in developing countries, high cost of medication may further prevent the initiation of proper treatment.

In recent years, scientific evidence has accumulated, showing that bariatric surgery can reverse type 2 diabetes, with evidence from studies over the past more than 10 years that resolution of type 2 diabetes is often observed as an additional outcome of surgical treatment of morbid obesity.

Many of these studies have also shown that diabetes-related morbidity and mortality declines significantly postoperatively, and that this improvement in diabetes control is long lasting. Bypass procedures, particularly the Roux-en-Y gastric bypass (RYGBP) and the biliopancreatic diversion (BPD), have proven more effective treatments for diabetes, as compared to other procedures and are associated with normalization of plasma glucose, insulin, and Glycated hemoglobin levels in more than 80% of morbidly obese patients undergoing these procedures (Buchwald H, Estok R, Fahrbach K, et al. Weight and type 2 diabetes after bariatric surgery: systematic review and meta-analysis. Am J Med 2009; 122:248-256, e5).

Studies indicate that these effects are nearly immediate, taking effect within hours or days after surgery, and are therefore not principally caused by longer-term weight-loss. The exact causes are unknown, but current hypothesis are for example: decreased absorption or partial malabsorption of nutrients, or anatomical alteration of the gastrointestinal tract causing a changed dynamic behavior of the incretin system.

Recently several studies report that invasive or noninvasive implantation of a sleeve in the small intestine, covering an initial intestine segment just beyond the stomach, can quickly improve glycemic control in obese diabetes patients.

For example, a small study of patients that received a duodenal-jejunal bypass liner implant (EndoBarrier™), reported that fasting plasma glucose levels fell 55 mg/dL, while levels among those who had a non-effective control procedure rose. The positive results proved to not be lasting over a period of a year, in part due to complications causing need for removal before trial expiration. (Rodriquez L, et al "Pilot clinical study of an endoscopic, removable duodenal-jejunal bypass liner for the treatment of type 2 diabetes" Diabetes Tech & Therapeutics 2009; DOI: 10.1089/dia.2009.0063.).

However, despite positive impact on diabetes from bypass bariatric surgery and intestinal sleeve procedures, significant morbidity and mortality risks are directly associated with such invasive surgical or device implantation procedures.

As such, considering the foregoing, it may be appreciated that there continues to be a need for novel and improved pharmaceutical compositions and methods for treating diabetes.

SUMMARY OF THE INVENTION

The foregoing needs are met, to a great extent, by the present invention, wherein in aspects of this invention, enhancements are provided to existing models of diabetes treatment with implanted sleeves, by a pharmaceutical composition and method of treatment that achieves similar results, without the considerable morbidity and mortality risks associated with past devices, procedures, and methods.

In an aspect, a pharmaceutical composition to be used as an oral medication, for the treatment of diabetes mellitus can include an antacid agent, and an enteric coating. The enteric coating permits the antacid agent to be delivered in the small intestine where it reduces acidity and thereby, according to findings and studies reported herein, causes a lowering of blood sugar levels.

In a related aspect, the pharmaceutical composition can be packaged in tablets, wherein the enteric coating forms a single shell, covering the antacid agent.

In a further related aspect, the pharmaceutical composition can be packaged in multiple-pellet tablets, wherein a tablet contains a plurality of individual pellets, which each contains a small amount of antacid agent coated by an enteric coating. This multiple-pellet tablet form can allow an enhanced distribution of the antacid agent in the small intestine. Furthermore, it can allow for improved control of the distribution pattern throughout the small intestine, by controlling the proportion of pellets with varying thickness of the enteric coating.

In another aspect, the pharmaceutical composition can further include an enteric-coated gastric acid secretion inhibitor, and can be packaged in various tablet forms.

In yet another aspect, the pharmaceutical composition can further include a composition for oral treatment of diabetes, such as metformin, in enteric or non-enteric delivery formulation.

In an aspect, a method for the treatment of diabetes in mammals and humans, can comprise administering to a host in need thereof a therapeutically effective amount of the pharmaceutical composition, in a daily dosage, or in multiple daily dosages.

DETAILED DESCRIPTION

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide example constructions. The embodiments are permissive rather than mandatory and illustrative rather than exhaustive.

Figure 1:
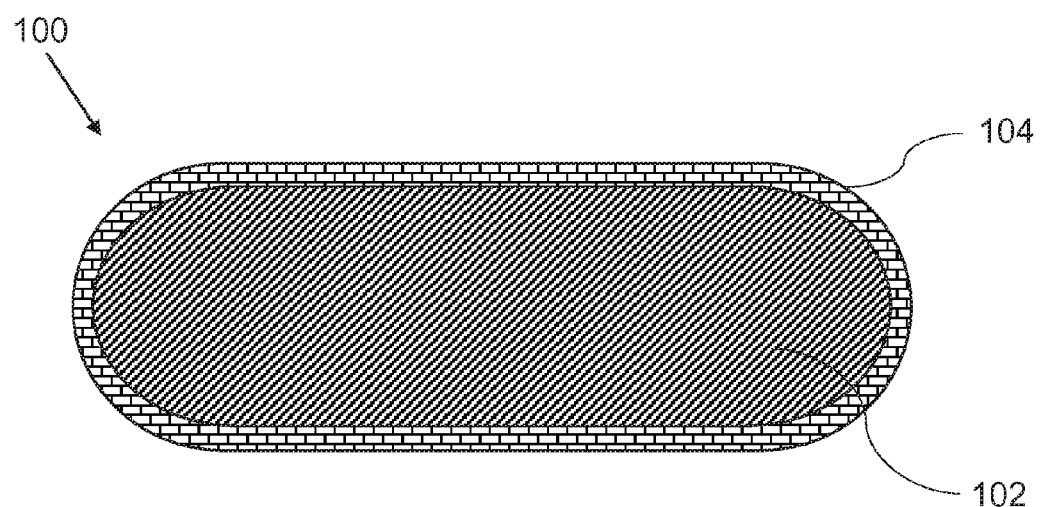
FIG. 1 is a cross-sectional view of a standard tablet, according to an embodiment of the invention.

In an embodiment, illustrated in FIG. 1, a pharmaceutical composition 100, to be used as an oral medication, for the treatment of diabetes mellitus, can be comprised of:
  a. an antacid agent 102; and
  b. an enteric coating 104;
  wherein the antacid agent 102 is coated by the enteric coating 104, and upon oral ingestion in a human host is delivered to the small intestine, and thereby reduces acidity, increasing the pH level of the small intestine, whereby the antacid agent 102 can effectuate a lowering of blood sugar levels of the human host.

In a related embodiment, the antacid agent 102 can include standard antacids such as:
  a. Aluminum hydroxide;
  b. Calcium carbonate;
  c. Magnesium hydroxide;
  d. Magnesium carbonite; or
  e. Aluminum magnesium hydroxide carbonate (hydrotalcite);
  or a combination of these;
  Wherein the dosage of the antacid agent 102 is substantially the well-known effective dosage for usage of the antacid agent 102 without an enteric coating.

In a further related embodiment, the antacid agent 102 can include alginates, for example alginic acid or sodium alginate or other pharmaceutically acceptable alginate salts, hydrates, esters, etc. The antacid agent 102 can thus also include combinations of one or more standard antacids with one or more alginates.

In a further related embodiment, the antacid agent 102 can include the active ingredients of well-known antacid brands, herein included:
  a. $NaHCO_3$ and/or $KHCO_3$ (Alka-Seltzer);
  b. $CaCO_3$ $MgCO_3$ (Andrews Antacid);
  c. $NaHCO_3$ (Brioschi);
  d. $CaCO_3$ $Al(OH)_3$ and $Mg(OH)_2$ (Equate);
  e. $Al(OH)_3$ and $Mg(OH)_2$ (Maalox, liquid);
  f. $CaCO_3$ (Maalox, tablet);
  g. $Mg(OH)_2$ (Milk of Magnesia);
  h. $C7H_5BiO_4$ (Pepto-Bismol);
  i. $CaCO_3$ (Pepto-Bismol Children's);
  j. $CaCO_3$ $MgCO_3$ (Rennie, tablets);
  k. $CaCO_3$ and $Mg(OH)_2$ (Rolaids);
  l. $CaCO_3$ (Tums);
  m. $Al(OH)_3$ $Mg(OH)_2$ $(C_2H_6OSi)_n \cdot (SiO_2)_m$ (Mylanta);
  n. $NaHCO_3$, Citric acid, $Na_2CO_3$ (Eno);
  o. $Al(OH)_3$ $Mg(OH)_2$ $(C_2H_6OSi)_n \cdot (SiO_2)_m$ (Gelusil);
  p. $CaCO_3$, $NaHCO_3$ and E401 Sodium alginate (Gaviscon);
  or a combination of these.

In a related embodiment the enteric coating 104 can include well-known enteric coatings, including:
  a. alcohol-based solutions of various types of food grade shellac, commonly referred to as pharmaceutical glaze;
  b. methyl acrylate-methacrylic acid copolymers;
  c. cellulose acetate succinate;
  d. hydroxy propyl methyl cellulose phthalate
  e. hydroxy propyl methyl cellulose acetate succinate (hypromellose acetate succinate)
  f. polyvinyl acetate phthalate (PVAP)
  g. methyl methacrylate-methacrylic acid copolymers
  h. Sodium alginate and stearic acid In a related embodiment, the enteric coating can be manufactured to form a single shell, entirely covering the antacid agent 102, wherein the single shell enteric coating and the antacid form a tablet 100. The tablet 100 can further be covered by an outer coating, such as a colored sugar coating, in order to eliminate any unpleasant taste sensation.

In a further related example embodiment, a tablet 100 can be manufactured such that the antacid agent 102 is calcium carbonate in a range of 300 mg to 900 mg.

Figure 2:
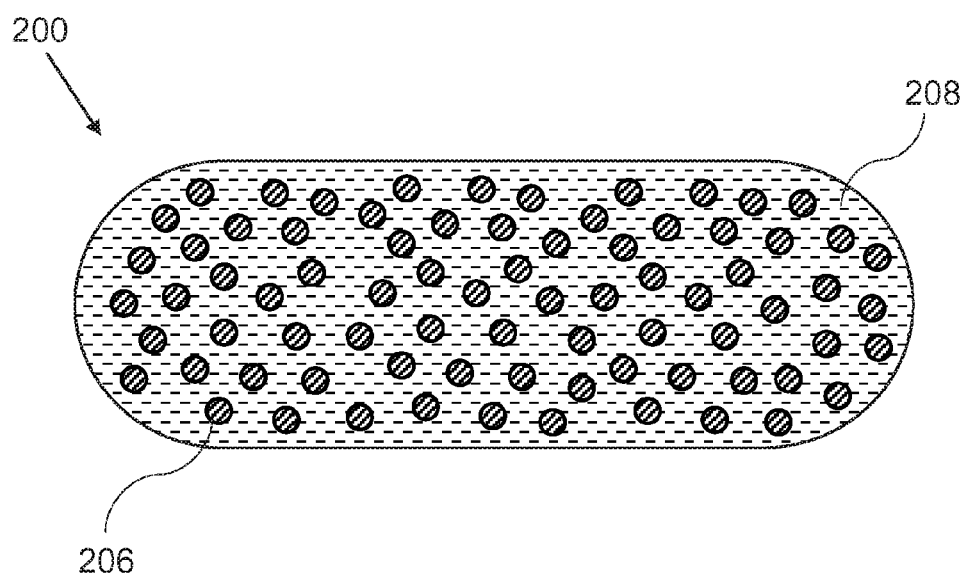
FIG. 2 is a cross-sectional view of a multiple-pellet tablet, according to an embodiment of the invention.
Figure 3:
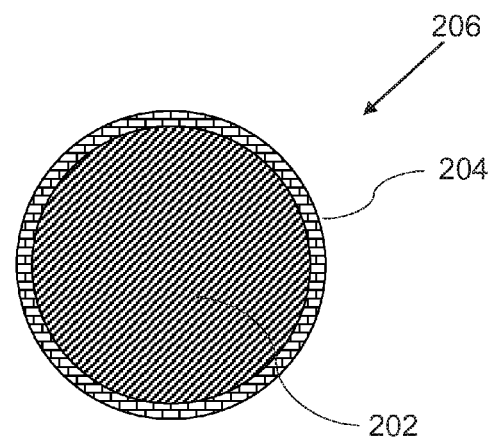
FIG. 3 is a cross-sectional view of a pellet, according to an embodiment of the invention.

In a related embodiment, illustrated in FIG. 2, a tablet for oral ingestion 200 can be formed of a large plurality of individual pellets 206, wherein each pellet 206, as illustrated in FIG. 3, is composed of a relatively small amount of the antacid agent 202, coated with the enteric coating 204, such that the total amount of the antacid agent 202 aggregates to a pharmaceutically effective amount when released in the small intestine. The pellets 206 can be embedded within a pharmaceutical excipient 208, and can be further encapsulated within a pharmaceutical film non-enteric coating.

In a related embodiment, FIG. 3 illustrates a pellet 206, further including an antacid agent 202, which is coated with the enteric coating 204.

A pellet shall be understood to mean a small bead, granule, or pellet. Pellets typically have a standardized size between 0.1 and 4 mm, but this may vary according to pharmaceutical application, in accordance with common knowledge in the field.

In a further related embodiment, the pellets 206 can be manufactured with a discrete set of pellet classes, wherein each pellet class has a different coating thickness of the enteric coating for each pellet, whereby the pellets 206 in each pellet class can be manufactured to release the antacid agent 202 after a specific amount of minutes exposure to the fluids in the small intestine. In this manner, a tablet 200 could for example be designed with a uniform delivery distribution to release 5% of its antacid contents for each 6 minutes of transit time in the small intestine, whereby delivery of the antacid would be approximately uniformly distributed throughout the length of the small intestine.

Figure 4:
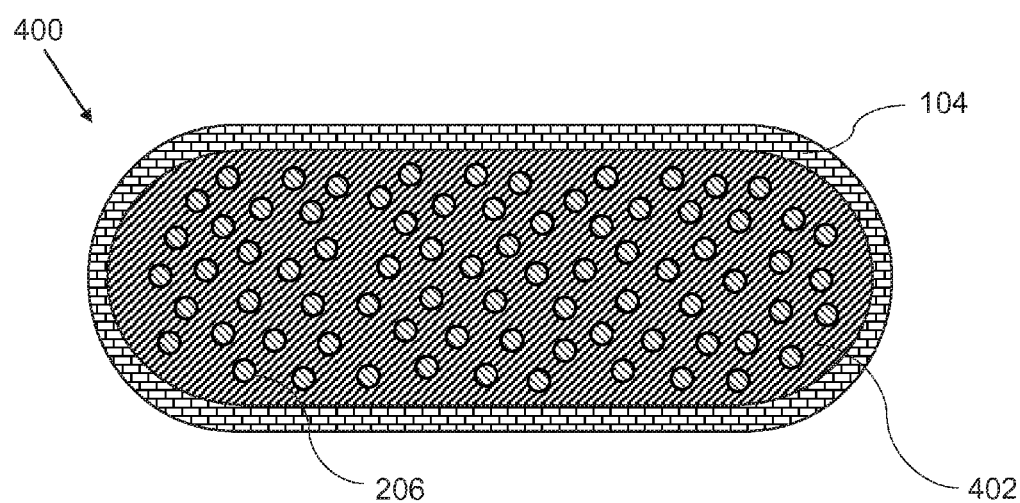
FIG. 4 is a cross-sectional view of a composite tablet with embedded pellets, according to an embodiment of the invention.

In a further related embodiment, as illustrated in FIG. 4, a compound tablet 400 for oral ingestion, can be composed of a first enteric coating 104, completely coating a pharmaceutically effective amount of a first antacid agent 402, wherein is further embedded a plurality of individual pellets 206, each coated with a second enteric coating 204, and each containing a relatively small amount of a second antacid agent 202, such that the total amount of the second antacid 202 aggregates to a pharmaceutically effective amount when released in the small intestine.

In a further related embodiment, such a compound tablet 400 can be manufactured with a first enteric coating 104 that dissolves immediately upon entry or very rapidly in the small intestine, such that the first antacid agent 402 is delivered immediately in the beginning of the small intestine, and the second antacid agent 202 is delivered according to a delivery distribution, across substantially the entire small intestine.

Figure 5:
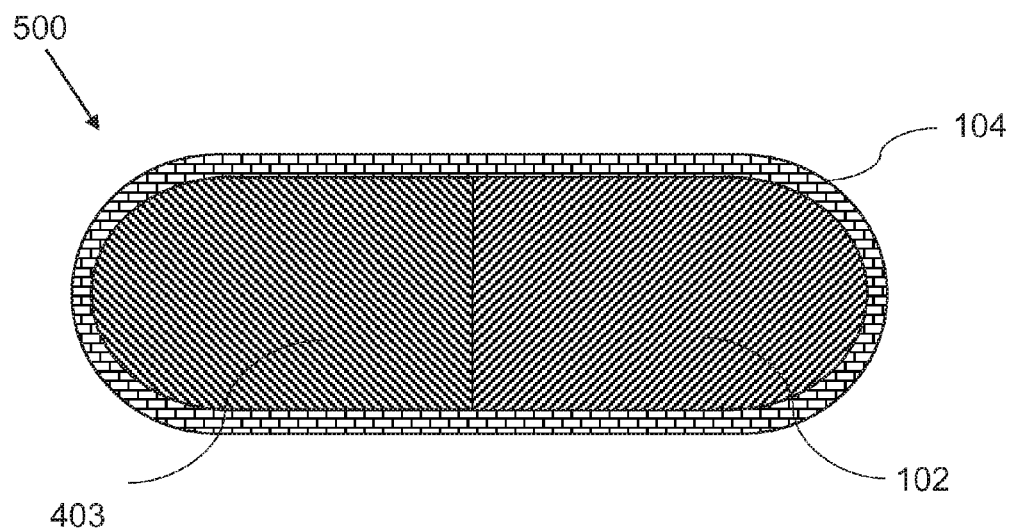
FIG. 5 is a cross-sectional view of a combination tablet, according to an embodiment of the invention.

In another embodiment, as illustrated in FIG. 5, a pharmaceutical combination composition 500, to be used as an oral medication, for the treatment of diabetes mellitus, can be comprised of:
  a. an antacid agent 102;
  b. a gastric acid secretion inhibitor 403; and
  c. an enteric coating 104;
  wherein the enteric coating 104 covers both the antacid agent 102 and the gastric acid secretion inhibitor 403, and upon oral ingestion in a human host both the antacid agent 102 and the gastric acid secretion inhibitor 403 is delivered to the small intestine, directly and indirectly increasing the pH level of the small intestine, whereby the oral medication can effectuate a lowering of blood sugar levels of the human host.

In a related embodiment, the gastric acid secretion inhibitor 403 can be a H2-receptor antagonist, such as for example Ranitidine, Cimetidine, Famotidine, or a combination of these.

In a related embodiment, the gastric acid secretion inhibitor 403 can be a proton-pump inhibitor such as for example: Omeprazole, Lansoprazole, Dexlansoprazole, Esomeprazole, Pantoprazole, Rabeprazole, Ilaprazole, or a combination of these.

In a related embodiment, the gastric acid secretion inhibitor 403 can be a combination of one or more H2-receptor antagonists and one or more proton-pump inhibitors.

In a related embodiment of the pharmaceutical combination composition 500, the enteric coating 104 can be manufactured to form a single shell, entirely covering the antacid agent 102 and the gastric acid secretion inhibitor 403, wherein the single shell enteric coating 104, the antacid agent 102, and the gastric acid secretion inhibitor 403 form a tablet 500. The tablet 500 can further be covered by an outer coating, such as a colored sugar coating, in order to eliminate any unpleasant taste sensation.

In a further related example embodiment, a tablet 500 can be manufactured such that the antacid agent 102 is calcium carbonate in a range of 300 mg to 900 mg, and the gastric acid secretion inhibitor 403 is omeprazole, an alkaline salt of omeprazole, a single enantiomer of omeprazole or an alkaline salt of the single enantiomer, in a range of 10 mg to 40 mg.

In a further related example embodiment, a single dosage form of a pharmaceutical composition or tablet 400 500 can be manufactured such that the antacid agent 102 is calcium carbonate in a range of 300 mg to 2000 mg, and the gastric acid secretion inhibitor 403 is omeprazole, an alkaline salt of omeprazole, a single enantiomer of omeprazole or an alkaline salt of the single enantiomer, in a range of 2.5 mg to 10 mg.

In a further related embodiment of the pharmaceutical combination composition, the antacid agent 102 can be packaged as a plurality of pellets 206, embedded in a pharmaceutical excipient.

In a further related embodiment of the pharmaceutical combination composition, the antacid agent 102 can be packaged as a plurality of pellets 206, embedded in a pharmaceutical excipient.

Figure 6:
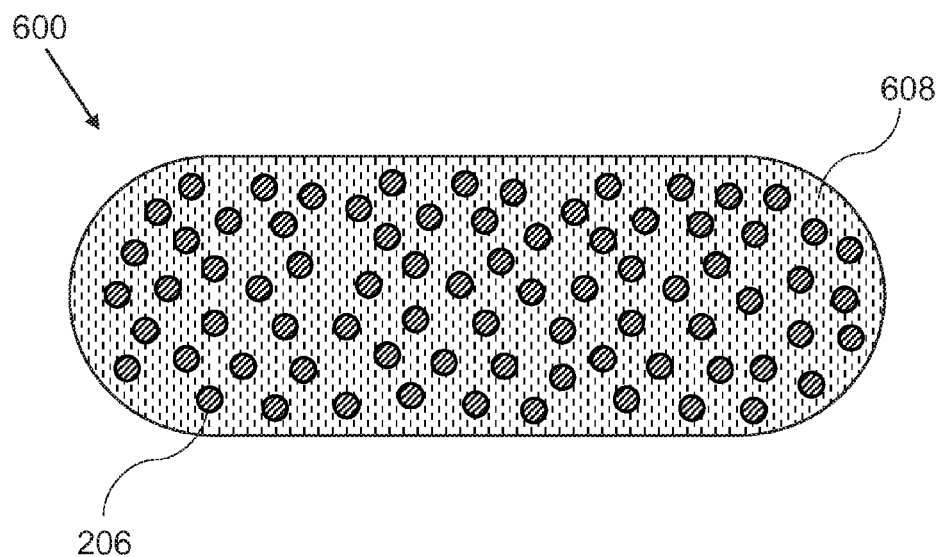
FIG. 6 is a cross-sectional view of a multiple-pellet tablet, according to an embodiment of the invention.

In an embodiment, as illustrated in FIG. 6, a combination tablet 600 for oral ingestion can include:
  a. a large plurality of individual pellets 206, wherein each pellet 206 is composed of a relatively small amount of the antacid agent 202, coated with the enteric coating 204, such that the total amount of the antacid agent 202 aggregates to a pharmaceutically effective amount when released in the small intestine;
  b. A composition for treatment of diabetes 608, wherein the pellets 206 are embedded, which can be further encapsulated within a pharmaceutical film non-enteric coating;
  Whereby the antacid agent 202 can work in conjunction with the composition for treatment of diabetes 608 to lower blood sugar levels of a human host, upon ingestion of the combination tablet 600 by the human host.

In a related embodiment, the composition for oral treatment of diabetes 608 can be an active ingredient selected from the group consisting of
  a. a biguanide, including metformin;
  b. a sulfonylurease, including chlorpropamide, glibenclamide, glyburide, glipizide, and glimepiride;
  c. a meglinitide, including repaglinide and nateglinide;
  d. a thizolidinedione, including rosiglitazone and pioglitazone;

e. a DPP-4 inhibitor, including sitagliptin, saxagliptin, and linagliptin;
f. a GLP-1 receptor agonist, including exenatide and liraglutide;
g. a SGLT2 inhibitor, including canagliflozin and dapagliflozin;
h. an alpha-glucosidase inhibitor, including acarbose and meglitol;
i. an insulin composition for oral ingestion, including ORMD-0801™; and
j. combinations thereof.

In various related embodiments, a specific composition for oral treatment of diabetes 608 has a therapeutically effective amount or dosage that is well known for those skilled in the art of diabetes treatment with pharmaceutical compositions and medications.

In a related embodiment, the composition for oral treatment of diabetes 608 can further include various well-known inactive ingredients, also referred to as pharmaceutical excipients, including fillers, binders, dyes, preservatives, flavoring agents, and combinations thereof.

Figure 7:
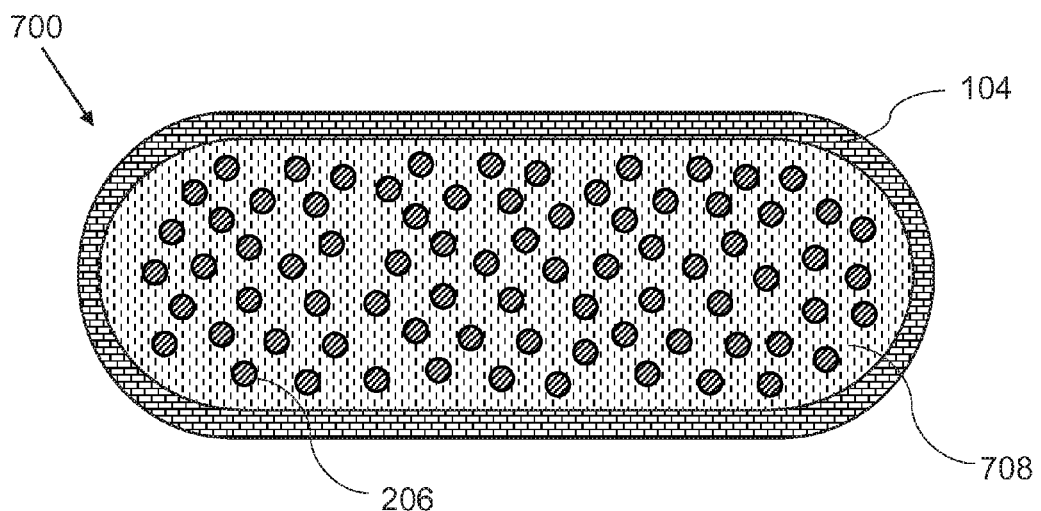
FIG. 7 is a cross-sectional view of a composite tablet with embedded pellets, according to an embodiment of the invention.
Figure 8:
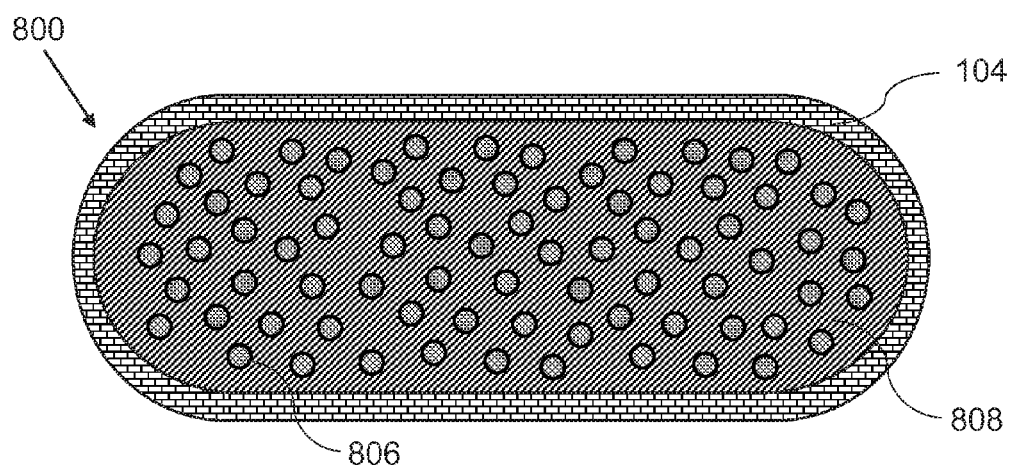
FIG. 8 is a cross-sectional view of a composite tablet with embedded pellets, according to an embodiment of the invention.

In a further related embodiment, as illustrated in FIG. 7, a compound tablet 700 for oral ingestion, can include:
a. a first enteric coating 104,
b. a pharmaceutically effective amount of a composition for treatment of diabetes 708, which is coated by the first enteric coating 104;
c. a plurality of individual pellets 206, embedded in the composition for treatment of diabetes 708, wherein each pellet 206 is coated with a second enteric coating 204, and each containing a relatively small amount of an antacid agent 202, such that the total amount of the antacid agent 202 aggregates to a pharmaceutically effective amount when released in the small intestine.

In a further related embodiment, such a compound tablet 700 can be manufactured with a first enteric coating 104 that dissolves immediately upon entry or very rapidly in the small intestine, such that the first antacid agent 402 is delivered immediately in the beginning of the small intestine, and the second antacid agent 202 is delivered according to a delivery distribution, across substantially the entire small intestine.

In a further related embodiment, a compound tablet 800 for oral ingestion, can include:
a. a first enteric coating 104,
b. an antacid agent 808, which is coated by the first enteric coating 104;
c. a plurality of individual pellets 806, embedded in the antacid agent 808, wherein each pellet 806 is coated with a second enteric coating 204, and each containing a relatively small amount of a composition for treatment of diabetes 608, such that the total amount of the composition for treatment of diabetes 608 aggregates to a pharmaceutically effective amount.

In a yet further related embodiment, such a compound tablet 800 can be manufactured with a first enteric coating 104 that dissolves immediately upon entry or very rapidly in the small intestine, such that the antacid agent 808 is delivered immediately in the beginning of the small intestine, and the composition for treatment of diabetes 608 is delivered according to an extended release predetermined delivery distribution, across substantially the entire small intestine.

Figure 9:
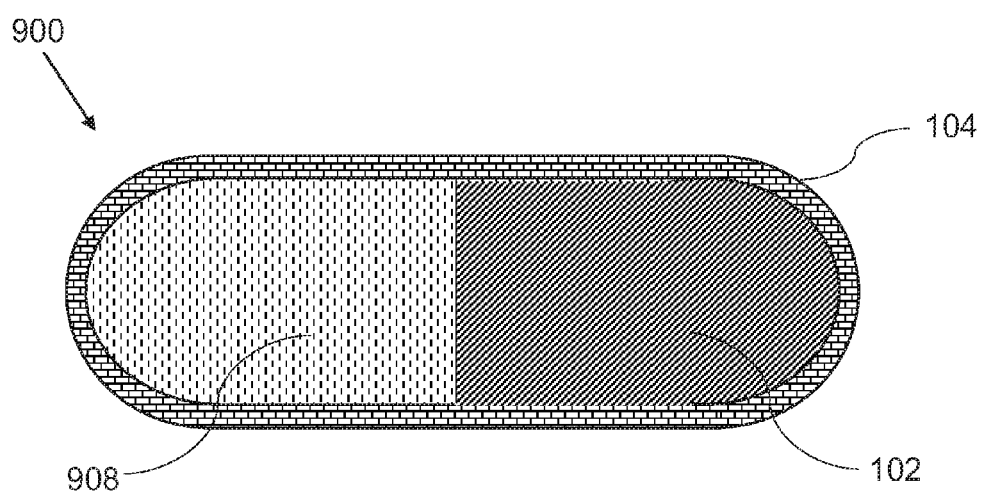
FIG. 9 is a cross-sectional view of a combination tablet, according to an embodiment of the invention.

In another embodiment, as illustrated in FIG. 9, a pharmaceutical combination composition 900, to be used as an oral medication, for the treatment of diabetes mellitus, can be comprised of:

a. an antacid agent 102;
b. a composition for treatment of diabetes 908; and
c. an enteric coating 104;
wherein the enteric coating 104 covers both the antacid agent 102 and the composition for treatment of diabetes 908, and upon oral ingestion in a human host both the antacid agent 102 and the composition for treatment of diabetes 908 is delivered to the small intestine, whereby the oral medication can effectuate a lowering of blood sugar levels of the human host.

In an embodiment, a method for the treatment of diabetes in mammals and humans can comprise administering to a host in need thereof a therapeutically effective amount of a pharmaceutical composition, wherein the pharmaceutical composition can be:
a. a pharmaceutical composition 100;
b. a tablet 200;
c. a compound tablet 400;
d. a pharmaceutical combination composition 500 or tablet 500;
e. a combination tablet 600;
f. a compound tablet 700;
g. a compound tablet 800; or
h. a pharmaceutical combination composition 900;
i. or a daily multi-dosage combination of one or several of a.-h.
wherein the pharmaceutical composition can be used as an oral medication.

In various related embodiments, a single-dosage form can include a single tablet dosage form of a pharmaceutical composition 100 200 400 500 600 700 800 900.

In a related embodiment, a method for the treatment of diabetes in humans can include use of a single-dosage form, such as a single tablet dosage form, of enteric calcium carbonate in a pharmaceutical composition 100 200 400 500 600 700 800 900 in a range of 300 to 2000 mg, such that a daily dosage can be in a range of 1200-8000 mg.

In a related embodiment, a method for the treatment of diabetes in humans can include 4 daily dosages of a pharmaceutical composition 100 200 400 500 600 700 800 900, such that each dosage is taken by a human host in need thereof, respectively before breakfast, before lunch, before dinner, and before sleeping.

In a related embodiment, a method for the treatment of diabetes in humans can include 4 daily dosages of enteric calcium carbonate in a pharmaceutical composition 100 200 400 500 600 700 800 900, such that each dosage is taken by a human host in need thereof, respectively before breakfast, before lunch, before dinner, and before sleeping.

In a further related example embodiment, a single dosage form of a pharmaceutical composition or tablet 600 700 800 900 can include the antacid agent as calcium carbonate in a range of 300-2000 mg and the composition for treatment of diabetes as metformin in a range of 125 mg to 1000 mg. In alternative related embodiments, the range of metformin can be 125-250, 125-500, 125-600, 125-750, or 125-850 mg.

Various embodiments of the present invention relate to the compositions and their associated methods of use, as described below.

Item 1: A pharmaceutical composition, to be used as an oral medication, for the treatment of diabetes mellitus, comprised of:
a. an antacid agent;
b. an enteric coating; and
c. metformin
wherein the antacid agent is coated by the enteric coating, whereby the pharmaceutical composition upon oral ingestion in a human host is delivered to the small intestine, and thereby reduces acidity, increasing the pH level of the small intestine, whereby the antacid agent in conjunction with the metformin effectuates a lowering of blood sugar levels of the human host.

Item 2: The pharmaceutical composition of item 1, wherein the antacid agent is selected from the group consisting of aluminum hydroxide, calcium carbonate, magnesium hydroxide, magnesium carbonate, aluminum magnesium hydroxide carbonate, and combinations thereof.

Item 3: The pharmaceutical composition of item 1, wherein the antacid agent further includes a pharmaceutical excipient.

Item 4: The pharmaceutical composition of item 1, wherein the enteric coating is manufactured to form a single shell, entirely covering the antacid agent, wherein the single shell enteric coating and the antacid agent form a tablet.

Item 5: The pharmaceutical composition of item 1, wherein the antacid agent includes calcium carbonate in a range of 300 mg to 900 mg.

Item 6: The pharmaceutical composition of item 1, wherein a tablet for oral ingestion is formed of a large plurality of individual pellets, wherein each pellet is composed of an amount of the antacid agent, coated with the enteric coating, such that the total amount of the antacid agent aggregates to a pharmaceutically effective amount for delivery in the small intestine.

Item 7: The pharmaceutical composition of item 6, wherein the pellets are manufactured with a discrete set of pellet classes, wherein each pellet class has a different coating thickness of the enteric coating for each pellet, whereby the pellets in each pellet class are manufactured to release the antacid agent after a specific amount of minutes exposure to fluids in the small intestine.

Item 8: The pharmaceutical composition of item 1, wherein the enteric coating includes a first enteric coating and a second enteric coating, and the antacid agent includes a first antacid agent and a second antacid agent, wherein further the first enteric coating is completely coating a pharmaceutically effective amount of the first antacid agent, such that a plurality of individual pellets is embedded in the first antacid agent, such that each pellet contains an amount of the second antacid agent inside a coating of the second enteric coating, such that the total amount of the second antacid agent aggregates to a pharmaceutically effective amount.

Item 9: The pharmaceutical composition of item 8, wherein the first enteric coating is configured to dissolve immediately upon entry into the small intestine, whereby the first antacid agent is delivered immediately in the beginning of the small intestine, wherein further the second antacid agent is delivered according to a predetermined delivery distribution, whereby the second antacid is delivered across a pre-determined segment of the small intestine.

Item 10: The pharmaceutical composition of item 1, further comprising a gastric acid secretion inhibitor, wherein the enteric coating covers both the antacid agent and the gastric acid secretion inhibitor, whereby upon oral ingestion in a human host both the antacid agent and the gastric acid secretion inhibitor are delivered to the small intestine, directly and indirectly reducing the acidity level of the small intestine, and thereby effectuating a lowering of blood sugar levels of the human host.

Item 11: The pharmaceutical composition of item 10, wherein the gastric acid secretion inhibitor includes a H2-receptor antagonist.

Item 12: The pharmaceutical composition of item 10, wherein the gastric acid secretion inhibitor includes a proton-pump inhibitor.

Item 13: The pharmaceutical composition of item 10, wherein the antacid agent includes calcium carbonate in a range of 300 mg to 900 mg, and the gastric acid secretion inhibitor includes omeprazole, an alkaline salt of omeprazole, a single enantiomer of omeprazole, or an alkaline salt of the single enantiomer, in a range of 10 mg to 40 mg.

Item 14: The pharmaceutical composition of item 1, wherein the metformin is coated by the enteric coating.

Item 15: The pharmaceutical composition of item 1, wherein the metformin is not coated by the enteric coating.

Item 16: A pharmaceutical combination composition, to be used as an oral medication, for the treatment of diabetes mellitus, comprised of:
 a. an antacid agent;
 b. a gastric acid secretion inhibitor; and
 c. an enteric coating;
 wherein the antacid agent aggregates to an effective amount of at least 300 mg, and the gastric acid secretion inhibitor aggregates to no more than 40 mg,
 wherein the enteric coating covers both the antacid agent and the gastric acid secretion inhibitor, whereby upon oral ingestion in a human host both the antacid agent and the gastric acid secretion inhibitor is delivered to the small intestine, directly and indirectly reducing the acidity level of the small intestine, thereby effectuating a lowering of blood sugar levels of the human host.

Item 17: The pharmaceutical combination composition of item 16, wherein the gastric acid secretion inhibitor comprises a H2-receptor antagonist.

Item 18: The pharmaceutical combination composition of item 16, wherein the gastric acid secretion inhibitor comprises a proton-pump inhibitor.

Item 19: The pharmaceutical combination composition of item 16, wherein the antacid agent includes calcium carbonate in a range of 300 mg to 900 mg, and the gastric acid secretion inhibitor includes omeprazole, an alkaline salt of omeprazole, a single enantiomer of omeprazole or an alkaline salt of the single enantiomer, in a range of 10 mg to 40 mg.

Item 20: The pharmaceutical combination composition of item 16, wherein the enteric coating is manufactured to form a single shell, entirely covering the antacid agent and the gastric acid secretion inhibitor, wherein the single shell enteric coating, the antacid agent, and the gastric acid secretion inhibitor form a tablet.

Item 21: The pharmaceutical combination composition of item 20, wherein the antacid agent is packaged as a plurality of pellets.

Item 22: The pharmaceutical combination composition of item 20, wherein the gastric acid secretion inhibitor is packaged as a plurality of pellets.

Item 23: The pharmaceutical combination composition of item 16, wherein the antacid agent is selected from the group consisting of aluminum hydroxide, calcium carbonate, magnesium hydroxide, magnesium carbonate, aluminum magnesium hydroxide carbonate, and combinations thereof.

Item 24: The pharmaceutical combination composition of item 16, further comprising metformin.

Item 25: A method for the treatment of diabetes in mammals and humans by administering to a host in need thereof a therapeutically effective amount of a pharmaceutical composition according to item 1.

Item 26: The method of item 23, wherein the diabetes is a type 2 diabetes in humans.

Item 27: A pharmaceutical composition, to be used as an oral medication, for the treatment of diabetes mellitus, comprised of:

a. an antacid agent; and
b. an enteric coating;
wherein the antacid agent does not include calcium carbonate;
wherein the antacid agent does not include a composition of potassium bicarbonate and sodium bicarbonate;
wherein the antacid agent is the only active ingredient of the pharmaceutical composition; and
wherein the antacid agent is coated by the enteric coating, whereby the pharmaceutical composition upon oral ingestion in a human host is delivered to the small intestine, and thereby reduces acidity, increasing the pH level of the small intestine, whereby the antacid agent effectuates a lowering of blood sugar levels of the human host.

Item 28: A pharmaceutical composition, to be used as an oral medication, for the treatment of diabetes mellitus, comprised of:
a. an antacid agent; and
b. an enteric coating;
wherein the antacid agent does not include calcium carbonate;
wherein the antacid agent does not include a composition of potassium bicarbonate and sodium bicarbonate;
wherein the antacid agent does not include magnesium hydroxide;
wherein the antacid agent does not include magnesium oxide;
wherein the antacid agent is the only active ingredient of the pharmaceutical composition; and
wherein the antacid agent is coated by the enteric coating, whereby the pharmaceutical composition upon oral ingestion in a human host is delivered to the small intestine, and thereby reduces acidity, increasing the pH level of the small intestine, whereby the antacid agent effectuates a lowering of blood sugar levels of the human host.

The exact mechanisms of function for the embodiments disclosed herein, remain uncertain, but may be related to the mechanisms causing reversal of diabetes progression for patients with implanted intestinal sleeves. Results from limited studies show clear indications of lasting reversal of diabetes, and may indicate another pathogenic road to diabetes, as compared to the standard pathogenic path of resistance to insulin leading to longer term reduced pancreatic insulin production.

A mechanism of function may include that reduced acidity in the small intestine allows healing or otherwise enhances the function of receptors that control secretion of glucagon and insulin.

EXAMPLE STUDIES

In a limited one-person two-month study, a male type 2 diabetic patient, on continuing treatment with metformin with clinical indication for initiation of insulin treatment, adopted an adjunct treatment regimen of three times a day enteric coated capsules, containing 500 mg calcium carbonate for a total daily dosage of 1500 mg. At the conclusion of the study, the patient had experienced a significant decrease in fasting blood sugar from a pre-study average of 140 mg/dl to an average of 86 mg/dl in the second half of the study. The postprandial glucose level decreased from an average of 180-220 mg/dl to 120-130 mg/dl. A1C levels decreased from 8.9 to 7.5.

A subsequent two-person two-month limited study achieved similar results with significant reductions of fasting, preprandial, and postprandial glucose levels, which were reduced from diabetic to normal levels with the adjunct treatment Both studies showed some indication of reduced appetite with a possible effect of long-term weight loss. Most significantly, both studies reversed a long-term trend of continuing worsening diabetic disease for the patients under study.

Here has thus been described a multitude of embodiments of the pharmaceutical composition and methods related thereto, which can be employed in numerous modes of usage.

The many features and advantages of the multitude of embodiments of the pharmaceutical composition and associated methods for the treatment of diabetes mellitus are apparent from the detailed specification, and thus, it is intended by the appended claims to cover all such features and advantages of the invention, which fall within the true spirit and scope of the invention.

Many such alternative compositions and pharmaceutical tablet forms are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:

1. A method for the treatment of diabetes in mammals and humans, comprising administering to a host in need thereof a therapeutically effective amount of a pharmaceutical composition to be used as an oral medication, wherein the pharmaceutical composition comprises:
   a) an antacid agent;
   b) a composition for treatment of diabetes;
   c) a first enteric coating; and
   d) a second enteric coating;
   wherein the antacid agent is coated by the first enteric coating,
   such that a plurality of individual pellets is embedded in the antacid agent, such that each pellet contains an amount of the composition for treatment of diabetes inside a coating of the second enteric coating, such that a total amount of the composition for treatment of diabetes aggregates to a pharmaceutically effective amount;
   wherein the first enteric coating is configured to dissolve immediately upon entry to the small intestine, such that the antacid agent is delivered immediately upon entry of the small intestine;
   wherein the second enteric coating is configured for extended release, such that the composition for treatment of diabetes is delivered according to an extended release predetermined delivery distribution, whereby the composition for treatment of diabetes is delivered across a predetermined segment of the small intestine;
   whereby the pharmaceutical composition upon oral ingestion in the host is delivered to the small intestine, and thereby reduces acidity, increasing the pH level of the small intestine, whereby the antacid agent in conjunction with the composition for treatment of diabetes effectuates a lowering of blood sugar levels of the host.

2. The method for the treatment of diabetes in mammals and humans of claim 1, wherein the diabetes is a type 2 diabetes in humans and the host is a human.

3. The method for the treatment of diabetes in mammals and humans of claim 1, wherein the composition for treatment of diabetes is comprised of a therapeutically effective amount of metformin.

4. The method for the treatment of diabetes in mammals and humans of claim 1, wherein the antacid agent is selected from the group consisting of aluminum hydroxide, calcium carbonate, magnesium hydroxide, magnesium carbonate, aluminum magnesium hydroxide carbonate, and combinations thereof.

5. The method for the treatment of diabetes in mammals and humans of claim 1, wherein the antacid agent in a single-dosage form of the pharmaceutical composition includes calcium carbonate in a range from 300 mg to 2000 mg.

6. The method for the treatment of diabetes in mammals and humans of claim 1, wherein the composition for treatment of diabetes is selected from the group consisting of:
 biguanides, including metformin;
 thizolidinediones, including rosiglitazone and pioglitazone;
 SGLT2 inhibitors, including canagliflozin and dapagliflozin;
 alpha-glucosidase inhibitors, including acarbose and meglitol;
 insulin compositions for oral ingestion; and
 combinations thereof;
 wherein the pharmaceutical composition further comprises a gastric acid secretion inhibitor, wherein the first enteric coating covers both the antacid agent and the gastric acid secretion inhibitor, whereby upon oral ingestion in a human host both the antacid agent and the gastric acid secretion inhibitor are delivered to the small intestine, directly and indirectly reducing the acidity level of the small intestine, and thereby effectuating a lowering of blood sugar levels of the human host.

7. The method for the treatment of diabetes in mammals and humans of claim 6, wherein the gastric acid secretion inhibitor includes a proton-pump inhibitor.

8. The method for the treatment of diabetes in mammals and humans of claim 6, wherein the antacid agent in a single-dosage form of the pharmaceutical composition includes calcium carbonate in a range from 300 mg to 2000 mg, and the gastric acid secretion inhibitor in the single-dosage form of the pharmaceutical composition includes omeprazole, an alkaline salt of omeprazole, a single enantiomer of omeprazole, or an alkaline salt of the single enantiomer, in a range of 2.5 mg to 10 mg.

9. The method for the treatment of diabetes in mammals and humans of claim 1, wherein the antacid agent in a single-dosage form of the pharmaceutical composition includes calcium carbonate in a range from 300 mg to 2000 mg, and the composition for treatment of diabetes in the single-dosage form of the pharmaceutical composition includes metformin in a range of 125 - 1000 mg.

10. The method for the treatment of diabetes in mammals and humans of claim 1, wherein the host is a human, and wherein the pharmaceutical composition is administered in 4 daily dosages, such that each dosage is taken by the host, respectively before breakfast, before lunch, before dinner, and before sleeping.

11. A method for the treatment of diabetes in mammals and humans, comprising administering to a host in need thereof a therapeutically effective amount of a pharmaceutical composition to be used as an oral medication, wherein the pharmaceutical composition comprises:
 a) an antacid agent;
 b) a composition for treatment of diabetes; and
 c) an enteric coating;
 wherein the antacid agent is coated by the enteric coating;
 wherein the composition for treatment of diabetes is not coated by the enteric coating;
 whereby the antacid agent upon oral ingestion in the host is delivered to the small intestine, and thereby reduces acidity, increasing the pH level of the small intestine,
 whereby the antacid agent in conjunction with the composition for treatment of diabetes effectuates a lowering of blood sugar levels of the host.

12. The method for the treatment of diabetes in mammals and humans of claim 11, wherein the diabetes is a type 2 diabetes in humans and the host is a human.

13. The method for the treatment of diabetes in mammals and humans of claim 11, wherein the composition for treatment of diabetes is comprised of a therapeutically effective amount of metformin.

14. The method for the treatment of diabetes in mammals and humans of claim 11, wherein the antacid agent is selected from the group consisting of aluminum hydroxide, calcium carbonate, magnesium hydroxide, magnesium carbonate, aluminum magnesium hydroxide carbonate, and combinations thereof.

15. The method for the treatment of diabetes in mammals and humans of claim 11, wherein the antacid agent includes calcium carbonate in a range from 300 mg to 2000 mg.

16. The method for the treatment of diabetes in mammals and humans of claim 11, wherein the enteric coating is configured to dissolve immediately upon entry to the small intestine, whereby the antacid agent is delivered immediately upon entry of the small intestine.

17. The method for the treatment of diabetes in mammals and humans of claim 11, wherein the composition for treatment of diabetes is selected from the group consisting of:
 biguanides, including metformin;
 thizolidinediones, including rosiglitazone and pioglitazone;
 SGLT2 inhibitors, including canagliflozin and dapagliflozin;
 alpha-glucosidase inhibitors, including acarbose and meglitol;
 insulin compositions for oral ingestion; and
 combinations thereof;
 wherein the pharmaceutical composition further comprises a gastric acid secretion inhibitor, wherein the enteric coating covers both the antacid agent and the gastric acid secretion inhibitor, whereby upon oral ingestion in a human host both the antacid agent and the gastric acid secretion inhibitor are delivered to the small intestine, directly and indirectly reducing the acidity level of the small intestine, and thereby effectuating a lowering of blood sugar levels of the human host.

18. The method for the treatment of diabetes in mammals and humans of claim 17, wherein the gastric acid secretion inhibitor includes a proton-pump inhibitor.

19. The method for the treatment of diabetes in mammals and humans of claim 17, wherein the antacid agent in a single-dosage form of the pharmaceutical composition includes calcium carbonate in a range from 300 mg to 2000 mg, and the gastric acid secretion inhibitor in the single-dosage form of the pharmaceutical composition includes omeprazole, an alkaline salt of omeprazole, a single enantiomer of omeprazole, or an alkaline salt of the single enantiomer, in a range of 2.5 mg to 10 mg.

20. The method for the treatment of diabetes in mammals and humans of claim 11, wherein the antacid agent in a single-dosage form of the pharmaceutical composition includes calcium carbonate in a range from 300 mg to 2000 mg, and the composition for treatment of diabetes in the single-dosage form of the pharmaceutical composition includes metformin in a range of 125 - 1000 mg.

* * * * *